(12) United States Patent
Radmacher et al.

(10) Patent No.: US 9,052,303 B2
(45) Date of Patent: Jun. 9, 2015

(54) DEVICE FOR DETERMINING TOTAL CHLORINE IN LIQUIDS

(75) Inventors: Edmund Radmacher, Duren (DE); Klaus Moller, Eschweiler (DE); Jurgen Hoffmann, Duren (DE)

(73) Assignee: AXAGARIUS GmbH & Co. KG, Dueren (DE)

( * ) Notice: Subject to any disclaimer, the term of this patent is extended or adjusted under 35 U.S.C. 154(b) by 422 days.

(21) Appl. No.: 12/617,044

(22) Filed: Nov. 12, 2009

(65) Prior Publication Data

US 2010/0124516 A1    May 20, 2010

(30) Foreign Application Priority Data

Nov. 14, 2008    (DE) .................. 10 2008 057 471

(51) Int. Cl.
*G01N 21/75* (2006.01)
*G01N 31/22* (2006.01)
*G01N 33/52* (2006.01)
*G01N 21/78* (2006.01)

(52) U.S. Cl.
CPC .............. *G01N 31/224* (2013.01); *G01N 21/78* (2013.01)

(58) Field of Classification Search
CPC ... G01N 31/22; G01N 33/523; G01N 31/224; G01N 21/78; Y10S 435/97
See application file for complete search history.

(56) References Cited

U.S. PATENT DOCUMENTS

| | | | |
|---|---|---|---|
| 3,811,840 A | | 5/1974 | Bauer et al. |
| 5,045,283 A | * | 9/1991 | Patel .............................. 422/424 |
| 5,391,482 A | * | 2/1995 | Mangold ........................ 435/18 |
| 5,491,094 A | | 2/1996 | Ramana et al. |
| 5,888,758 A | * | 3/1999 | Wu ................................. 435/28 |
| 2005/0123439 A1 | * | 6/2005 | Patton et al. .................... 422/56 |

FOREIGN PATENT DOCUMENTS

| | | |
|---|---|---|
| DE | 2015271 | 10/1970 |
| DE | 2107879 | 4/1978 |
| EP | 0762120 | 5/2003 |
| EP | 1259798 | 4/2008 |
| GB | 1 333 442 | 10/1973 |
| WO | WO 0239081 A2 * | 5/2002 |

OTHER PUBLICATIONS

Laborbucher Chemie—Leonhard A. Hutter—Wasser and Wasseruntersuchung, 1992.

* cited by examiner

*Primary Examiner* — Dennis M White
*Assistant Examiner* — Bryan Kilpatrick
(74) *Attorney, Agent, or Firm* — Berenato & White, LLC

(57) ABSTRACT

A device is provided for determining total chlorine in liquids, the device including an indicator carrier that is impregnated with a color indicator that contains Michler's thioketone, the indicator carrier additionally containing as a color indicator at least one azine as well as an iodide, in particular potassium iodide and/or sodium iodide.

25 Claims, 1 Drawing Sheet understand # DEVICE FOR DETERMINING TOTAL CHLORINE IN LIQUIDS

CROSS-REFERENCE TO RELATED APPLICATIONS AND CLAIM TO PRIORITY

This application is related to application number 10 2008 057 471.6-52, filed Nov. 14, 2008, in the Federal Republic of Germany, the disclosure of which is incorporated by reference and to which priority is claimed.

FIELD OF THE INVENTION

The present invention relates to a device for determining the total chlorine content in a liquid, the device including an indicator carrier that contains Michler's thioketone as a color indicator. The invention further relates to a method for manufacturing such a device, the indicator carrier being impregnated with an impregnation solution that contains the color indicator.

BACKGROUND OF THE INVENTION

The existing art discloses test sticks for determining total chlorine content, in particular total chlorine quantities in the range from 0.1 to 3 ppm in water, in which an indicator carrier in the form of an indicator paper, made of filter paper, is mounted on a stick and impregnated with an indicator solution. Present in the indicator carrier is a color indicator which, expressly avoiding potassium iodide, is made up solely of Michler's thioketone, and which is combined with an ionic, fluorinated surface-active agent (cf. EP 1 259 798 B1, in particular Claim 1 and paragraph [0025]). The pH of the color indicator is adjusted to 3 to 8, by preference 5, by the addition of acid or basic substances. Stabilizers can additionally be added to the indicator solution.

With the aid of the test stick, the concentration of total chlorine can be ascertained semiquantitatively as follows: starting from a 0 ppm total chlorine content, the initially yellow color changes, with higher total chlorine content, through dark green at 0.5 ppm to blue at 3 ppm. The color that is established in each case can then be compared with a color comparison chart, and the respective total chlorine content can be identified based on the concentration values associated thereon with the colors.

Also known are test sticks for ascertaining free chlorine content in aqueous solutions (see Hütter, Wasser and Wasseruntersuchung [Water and water investigation], 5th ed., 1992, page 149 for a definition of free, bound, and total chlorine). In these test sticks certain azines, in particular syringaldazines and vanillin azines, are used as color indicators, their pH being adjusted by means of a buffer to a value of 3.5 to 8.5. These test sticks are not suitable for determining total chlorine content.

SUMMARY OF THE INVENTION

The object underlying the invention is that of embodying a device for determining the total chlorine content in a liquid so that it is notable for stability, a definite color change, and therefore high measurement accuracy. A further object is that of making available a method for manufacturing such a device.

This object is achieved according to the present invention in that the indicator carrier contains as a color indicator, in addition to Michler's thioketone, at least one azine as well as an iodide, in particular potassium iodide and/or sodium iodide. The fundamental idea of the invention is therefore to use at least two substances for the color indicator, namely Michler's thioketone and at least one azine, and to combine the color indicator with an iodide. Experiments have shown that an extraordinarily stable system that therefore ensures high measurement accuracy, with a clearly recognizable color change, has been discovered, which system is suitable chiefly for rapidly determining the total chlorine content in aqueous liquids, in particular for the range from 0.1 to 10 mg/l total chlorine content. The device is usefully embodied as test sticks having a layer made up of an absorbent matrix, for example filter paper, that is impregnated with an impregnation solution.

In an embodiment of the invention, provision is made that the color indicator is present in the indicator carrier at a concentration, and at a mixing ratio between Michler's thioketone and azine(s), such that the color developed upon immersion into a liquid having 0 mg/l total chlorine is yellow, and a color change through green to blue is produced as the total chlorine content rises to 10 mg/l.

The weight ratio of Michler's thioketone to azine(s) is usefully in the range from 1:5 to 1:20, preferably 1:12. The combination of the two color indicators achieves a particularly good effect in this range.

Syringaldazine or vanillin azine, preferably a combination of the two, is recommended as (an) azine(s). In that case the weight ratio between the two should be between 1:1 and 1:3, preferably 1:1.6.

With regard to the iodide, in particular potassium iodide or sodium iodide, it is useful if the iodide and the color indicator are present in the indicator carrier at a weight ratio from 1:1 to 1:3, preferably at a weight ratio of 1:2.3.

In order to optimize the stability of the color indicator, a stabilizer (for example, phenylsemicarbazide) should also be present in the indicator carrier. It is useful if the stabilizer and the color indicator are present in the indicator carrier at a weight ratio from 1:1 to 1:3, preferably 1:2.2.

A buffer substance should also be contained in the indicator carrier in order to adjust the pH of the color indicator. The pH should thereby be established in the range of 3 to 8, preferably of 4 to 6, even better of 5. The buffer substances can be phosphate salts, in that case preferably potassium dihydrogenphosphate and disodium hydrogenphosphate.

The second part of the object is achieved according to the present invention in that the indicator carrier is impregnated with at least one impregnation solution which contains at least one azine as an additional color indicator, and which contains an iodide, in particular potassium iodide. Syringaldazine and/or vanillin azine are suitable in this context as (an) azine(s). The weight ratio in the impregnation solution between them should be 1:1 to 1:3, preferably 1:1.6.

According to a further feature of the invention, provision is made that the indicator carrier is firstly impregnated with a first impregnation solution that contains the iodide; and that in a further step, preferably after drying of the indicator carrier, the indicator carrier is impregnated with a second impregnation solution that contains the color indicator. This procedure has proven advantageous.

DETAILED DESCRIPTION OF THE INVENTION

The iodide in the first impregnation solution can be dissolved in a mixture of distilled water and at least one alcohol, preferably ethanol. The volume proportion of alcohol in relation to water should be less than 50%, preferably 30%. The iodide is present in the first impregnation solution usefully at a weight proportion from 0.05 to 5 g/l, preferably 0.5 g/l.

Disodium hydrogenphosphate and/or potassium dihydrogenphosphate should also be dissolved in the first impregnation solution, and the pH of the first impregnation solution should be adjusted by means of an acid, in particular hydrochloric acid, to a pH of 3 to 8, preferably of 4 to 6, even better of 5.

In the second impregnation solution, the color indicator should be dissolved in acetone. The proportion of Michler's thioketone in the second impregnation solution should be 0.04 to 4 g/l, preferably 0.22 g/l. A stabilizer, for example phenylsemicarbazide, should additionally be introduced into the second impregnation solution. Said stabilizer should be added in a quantity from 0.04 to 4 g/l, preferably 0.1 g/l.

The procedure for manufacturing a test stick having the impregnation solution according to the present invention is, for example, as follows:

The following are dissolved in a mixture of 70 ml distilled water and 30 ml ethanol:
0.19 g disodium hydrogenphosphate,
1.03 g potassium dihydrogenphosphate, and
0.05 g potassium iodide.

The pH of the solution is then adjusted with hydrochloric acid to pH 5.0, and the indicator carrier, made up of a filter paper, is impregnated with this impregnation solution. The indicator carrier is then dried.

In a second step, the following are dissolved in 250 ml acetone:
0.25 syringaldazine,
0.40 vanillin azine,
0.055 g Michler's thioketone, and
0.025 g 1-phenylsemicarbazide.

The indicator carrier is likewise impregnated with this impregnation solution. After drying, the indicator carrier is adhesively bonded onto a test stick film.

Figure 1:
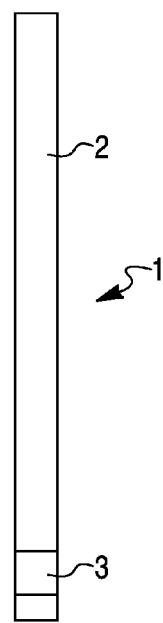
FIG. 1 is an elevational view of a device for determining total chlorine in liquids.
Figure 2:
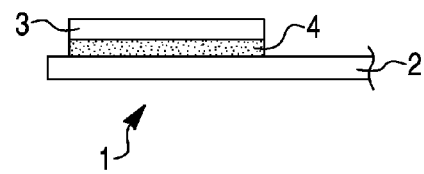
FIG. 2 is a fragmentary cross-sectional view of the device of FIG. 1.

An exemplifying embodiment is illustrated in the drawings. A test stick 1 is shown in FIGS. 1 and 2. Test stick 1 has a carrier stick 2 of rectangular outline, in the region of one of whose ends an indicator carrier 3 is attached by means of an adhesive layer 4. Indicator carrier 3 has been impregnated with the impregnation solutions described above by way of example.

In order to ascertain the total chlorine content in an aqueous liquid, test stick 1 is moved back and forth in the solution for 15 seconds. Indicator carrier 3 acquires a yellow/green color in the presence of total chlorine at 0.1 mg/l, dark green at 0.5 mg/l, and dark blue at 10 mg/l. By comparison with a color scale, the total chlorine content can be measured semiquantitatively in the concentration steps of 0.1, 0.5, 1, 3, and 10 mg/l. If no chlorine is present, the color of the indicator carrier is yellow.

We claim:

1. A device for determining total chlorine in liquids, the device comprising:
an indicator carrier impregnated with a color indicator that comprises Michler's thioketone, wherein the indicator carrier additionally contains as a further color indicator at least one azine and at least one iodide, and wherein the indicator carrier contains a phenylsemicarbazide stabilizer, wherein the color indicators are present at concentrations and a mixing ratio of the Michler's thioketone to the at least one azine such that the color developed under immersion of the indicator carrier into a liquid having a total chlorine content of a 0 mg/l is yellow and a color change through green to blue is produced as the total chlorine content of the liquid rises to 10 mg/l,
wherein the weight ratio of Michler's thioketone to the at least one azine is in a range from 1:5 to 1:20.

2. The device of claim 1, wherein the iodide comprises at least one member selected from the group consisting of potassium iodide and sodium iodide.

3. The device according to claim 1, wherein the device comprises a test stick comprising the indicator carrier, wherein the indicator carrier is an absorbent layer.

4. The device according to claim 1, wherein the at least one azine comprises at least one azine selected from the group consisting of syringaldazine and vanillin azine.

5. The device according to claim 4, wherein syringaldazine and vanillin azine are present at a weight ratio from 1:1 to 1:3.

6. The device according to claim 1, wherein the iodide and the at least one azine are present in the indicator carrier at a weight ratio from 1:1 to 1:3.

7. The device according to claim 1, wherein the phenylsemicarbazide stabilizer and the color indicators are present in the indicator carrier at a weight ratio from 1:1 to 1:3.

8. The device according to claim 1, wherein one or more buffer substances are present in the indicator carrier in order to adjust the pH of the color indicator to a pH of 3 to 8.

9. The device according to claim 8, wherein the buffer substances are phosphate salts.

10. The device according to claim 9, wherein the buffer substances comprise at least one member selected from the group consisting of potassium dihydrogenphosphate and disodium hydrogenphosphate.

11. A method for manufacturing a device for determining the total chlorine content in a liquid, the method comprising:
impregnating an indicator carrier with an impregnation solution which contains a color indicator that comprises Michler's thioketone, and
impregnating the indicator carrier with a further color indicator comprising at least one azine and at least one iodide, wherein the color indicators are present at concentrations and a mixing ratio of the Michler's thioketone to the at least one azine such that the color developed under immersion of the indicator carrier into a liquid having a total chlorine content of a 0 mg/l is yellow and a color change through green to blue is produced as the total chlorine content of the liquid rises to 10 mg/l,
wherein the weight ratio of Michler's thioketone to the at least one azine is in a range from 1:5 to 1:20,
wherein said impregnating comprises impregnating the indicator carrier with a first impregnation solution that contains the iodide and thereafter impregnating the indicator carrier with a second impregnation solution that contains the color indicators and a phenylsemicarbazide stabilizer.

12. The method according to claim 11, wherein the iodide comprises potassium iodide.

13. The method according to claim 11, wherein the at least one azine comprises at least one azine selected from the group consisting of syringaldazine and vanillin azine.

14. The method according to claim 13, wherein the weight ratio of syringaldazine to vanillin azine is 1:1 to 1:3.

15. The method according to claim 11, wherein the iodide of the first impregnation solution is dissolved in a mixture of distilled water and at least one alcohol.

16. The method according to claim 15, wherein the alcohol comprises ethanol.

17. The method according to claim 15, wherein the alcohol is present in a volume proportion in relation to water of less than 50%.

18. The method according to claim 11, wherein the iodide is present in the first impregnation solution at a weight proportion from 0.05 to 5 g/l.

19. The method according to claim 11, wherein disodium hydrogenphosphate and/or potassium dihydrogenphosphate is dissolved in the first impregnation solution.

20. The method according to claim 11, wherein the first impregnation solution is adjusted, by addition of phosphate salts and hydrochloric acid, to a pH in a range of 3 to 8.

21. The method according to claim 11, wherein the color indicators in the second impregnation solution are dissolved in acetone.

22. The method according to claim 11, wherein the Michler's thioketone is present in the second impregnation solution in proportion of 0.04 to 4 g/l.

23. The method according to claim 11, wherein the second impregnation solution contains 0.04 to 4 g/l of the phenylsemicarbazide stabilizer.

24. A method for determining the total chlorine content in a liquid, the method comprising:

contacting a device with a liquid, the device comprising an indicator carrier impregnated with a color indicator comprising Michler's thioketone, the indicator additionally containing as a further color indicator at least one azine and at least one iodide, wherein the color indicators are present at concentrations and a mixing ratio of the Michler's thioketone to the at least one azine such that the color developed under immersion of the indicator carrier into a liquid having a total chlorine content of a 0 mg/l is yellow and a color change through green to blue is produced as the total chlorine content of the liquid rises to 10 mg/l, wherein the weight ratio of Michler's thioketone to the at least one azine is in a range from 1:5 to 1:20; and observing a color change to the indicator carrier, wherein the indicator carrier contains a phenylsemicarbazide stabilizer.

25. The device of claim 1, wherein the concentrations of the color indicators and the mixing ratio are such that the colors developed under immersion of the indicator in liquids having total chlorine contents of 0.1 mg/l, 0.5 mg/l, and 10 mg/l are yellow-green, dark green, and dark blue, respectively.

* * * * *